United States Patent [19]

Silver

[11] Patent Number: 4,910,384
[45] Date of Patent: Mar. 20, 1990

[54] POSITION INDEPENDENT HUMIDIFIER APPARATUS

[75] Inventor: Brian H. Silver, Cary, Ill.

[73] Assignee: The Kendall Company, Boston, Mass.

[21] Appl. No.: 235,402

[22] Filed: Aug. 23, 1988

[51] Int. Cl.$^4$ .................. H05B 3/02; A61M 16/18; B01F 3/04

[52] U.S. Cl. ................. 219/271; 128/203.17; 261/101

[58] Field of Search .................. 219/271–276; 261/DIG. 65, 101, 102, 103; 128/204.13, 203.17, 203.16, 203.27, 204.17

[56] References Cited

U.S. PATENT DOCUMENTS

| | | | |
|---|---|---|---|
| 4,201,737 | 5/1980 | Carden | 219/275 |
| 4,355,636 | 10/1982 | Oetjen et al. | 261/DIG. 65 |
| 4,381,267 | 4/1983 | Jackson | 128/204.13 |
| 4,532,088 | 7/1985 | Miller | 219/273 |
| 4,657,713 | 4/1987 | Miller | 219/273 |
| 4,682,010 | 7/1987 | Drapeau et al. | 128/203.27 |
| 4,753,758 | 7/1988 | Miller | 219/275 |

FOREIGN PATENT DOCUMENTS

| | | | |
|---|---|---|---|
| 483086 | 4/1976 | Australia | 128/203.27 |
| 61-72948 | 4/1986 | Japan | 219/272 |
| 165534 | 7/1986 | Japan | 219/272 |

Primary Examiner—A. D. Pellinen
Assistant Examiner—Geoffrey S. Evans
Attorney, Agent, or Firm—Alvin Isaacs

[57] ABSTRACT

A humidification apparatus for utilization in human respiration systems comprising a hollow housing in which an envelope of vapor permeable water impermeable material is arranged to divide the housing generally in half. A heater and a water supply conduit are arranged in the envelope. A gas inlet and a gas outlet port are disposed through the housing and are in communication with each other. The heater changes the water into vapor and permits it to pass through the envelope and be carried with the gas, out of the housing to a patient.

25 Claims, 3 Drawing Sheets

FIG. 2
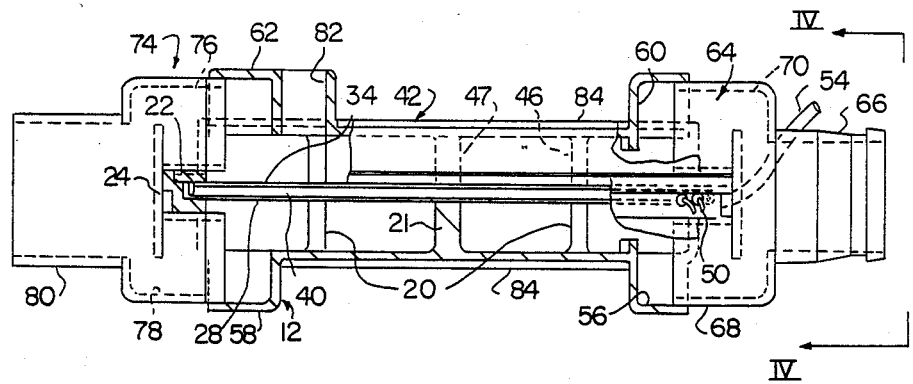
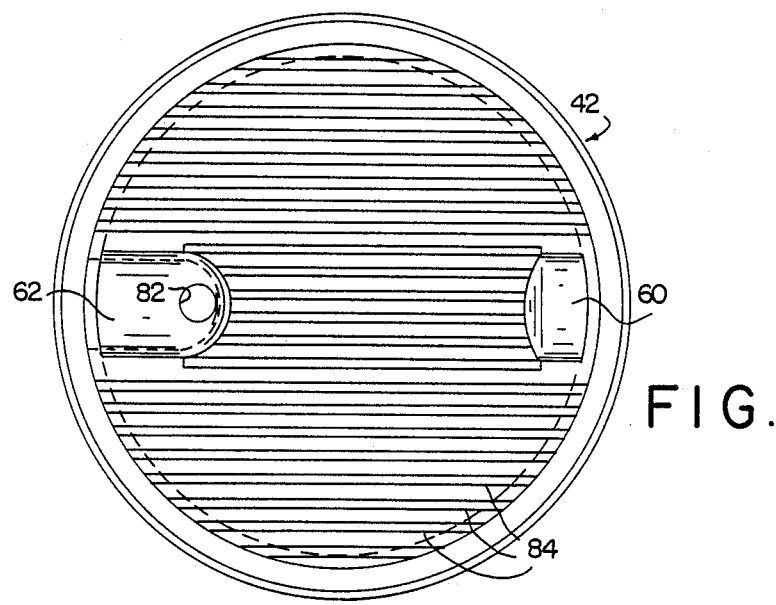
FIG. 3

POSITION INDEPENDENT HUMIDIFIER APPARATUS

BACKGROUND OF THE INVENTION

1. Field of the Invention

This invention relates to humidifiers, and more particularly to humidifiers for human respiration systems.

2. Prior Art

Humidification systems are useful devices when utilized in respiratory therapy or anesthesiology because they deliver humidified warmed gas to a patient.

One such humidifier system is shown in U.S. Pat. No. 4,532,088 to Miller wherein a horizontally disposed heater surface is adapted to receive liquid water from a source in a direct heat transfer relationship. The entire unit sits on a housing. This system does not readily facilitate juxaposition of the supply of heated humidified air to the patient which may aggrevate the temperature drop, moisture loss and increase water consumption.

A further humidification system which is typical in the art is shown in U.S. Pat. No. 4,629,590 to Bagwell wherein a nebulizer is secured to a liquid container to produce a stream of moisturized gas in a generally horizontal circumferential path around the inner surface of the container. Orientation of this device is critical, since any tipping thereof appears capable of flooding the patient.

A further example of the prior art is shown in U.S. Pat. No. 4,588,475 to Usry et. al., wherein a jet pump-like action is utilized to draw water from a reservoir and entrain it as a vapor in gas flowing through the apparatus for high frequency ventilation use. The positioning of a venturi in this system, below the water level in a self-contained reservoir, facilitates water pick-up here.

A position independent humidification system is needed, which will permit disposition close to the patient, thus reducing temperature drop, energy consumption, moisture loss and water consumption. None of the art has produced such a device.

It is an object of the present invention to provide a humidification and heating device for a human respiration system, which device is omnipositional, and which permits placement thereof in close proximity to a patient utilizing the device.

BRIEF SUMMARY OF THE INVENTION

The present invention provides a humidification assembly for improving the moisture and temperature of a breathable gas to be inhaled by a patient undergoing inhalation therapy. The humidifier assembly comprises a housing into which gas and water are supplied. The housing contains a heater element which heats and humidifies the gas which is then directed to a passageway to the patient.

The housing comprises a pair of generally flat disc shaped members each having a peripherally disposed wall which engage one another in an edge to edge relationship to define a chamber between the disc shaped housing members.

A round planar etched foil electrical heater is disposed across the chamber and has an absorbent wick-like material, such as paper, attached to at least one side thereof. The heater and wick paper are sandwiched into an enclosure of microporous membrane material, which permits the passage of only water vapor therethrough. The membranes are bonded adjacent the periphery of their respective walls of each housing portion during manufacture, so as to effectively comprise an envelope surrounding the heater, and to comprise a chamber on either side of the heater, between each membrane and its disc shaped housing portion.

A water supply conduit gravity feeds water from a water source to a discharge point at the heater surface within the membrane envelope so as to disperse water onto the heater surface and the wick material. The water is confined to the inside of the envelope because the membranes are sealed at their periphery, in a water tight relationship, to the mated walls of their housing portions.

The heater has electrical wires which extend in a water tight manner through the side wall of one of the housing portions which comprises the peripheral edge of the membrane envelope.

A gas supply conduit is received by an inlet at a point on the peripheral wall, having ducting means into each side chamber of the humidifying device. A gas outlet conduit is attachable to an outlet at a point on the peripheral wall diametrically opposite the inlet.

Controlled discharge of water through the water supply conduit onto the surface of the electrically energized heater element in the envelope and dispersal thereat by the wick material facilitates evaporation thereof. Then subsequent passage of the heated water vapor through the microporous membrane of the envelope heats and humidifies gas in the chambers. The gas supply passing into the chamber between the microporous membrane of the envelope and the disc-shaped walls of the housing picks up the heat and moisture treated vapor and carries it to the outlet diametrically across the housing, to the feed conduit leading to the patient.

BRIEF DESCRIPTION OF THE DRAWINGS

The objects and advantages of the present invention will become more apparent, when viewed in conjunction with the following drawings, in which:

FIG. 2 is a side-elevational view of the assembly, part of which is in section;

FIG. 3 is a plan view of one side of the housing of the assembly;

DESCRIPTION OF THE PREFERRED EMBODIMENT

Figure 1:
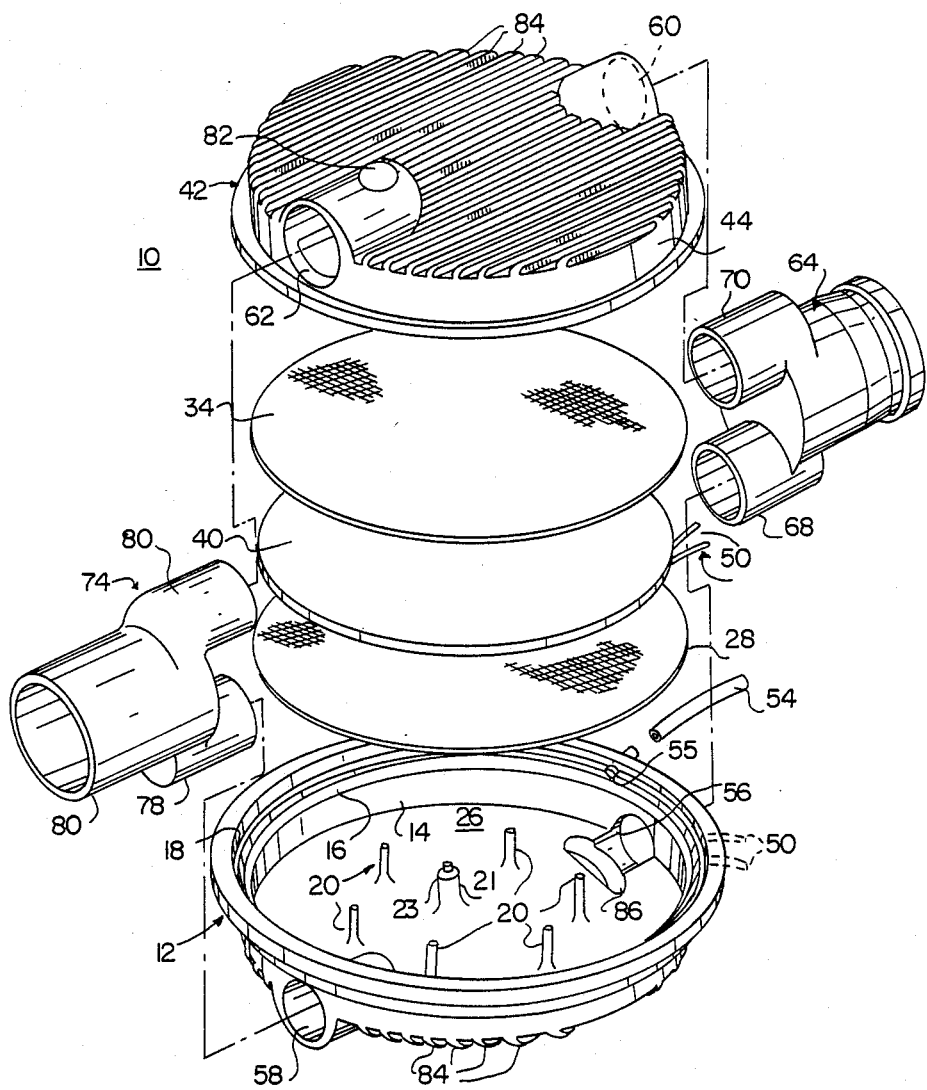
FIG. 1 is an exploded perspective view of humidification assembly constructed according to the principles of the present invention.

Referring now to the drawings in detail, and particularly to FIG. 1, there is shown in exploded representation, a humidification assembly 10 for use with an inhalation system, generally similar to that shown in my copending commonly assigned U.S. Patent Application PF 1671, entitled "Method for Humidifying a Breathable Gas", incorporated herein by reference.

The humidification assembly 10 comprises a first housing member 12 of generally circular disc-like configuration having a peripheral wall 14. The peripheral wall 14 has an annular shoulder 16 therearound. A peripheral lip 18 is disposed about the distal edge of the wall 14.

A plurality of standoffs 20, including a central standoff 21, are disposed off of the inside surface of the first housing member 12, as can be seen in FIGS. 1 and 2.

The standoffs 20 and 21 have a distal end which lies in the plane of the annular shoulder 16. A first, generally circular vapor permeable membrane 28, which is impermeable to liquids, is attached by known bonding means to the annular shoulder 16 around its entire periphery, in a hermetically sealed manner. The standoffs 20 and 21 in the first housing member 12 support the first membrane 28, to define a first flow chamber 26 between the first membrane 28 and the first housing 12, as shown in figures I and 2. The first membrane 28 is also preferably bonded to the distal end of each standoff 20, including the central standoff 21, which has a boss 23 which extends through a central opening in the first membrane 28, to facilitate positioning thereof during assembly.

A second housing member 42 of generally disc-like configuration has a peripheral wall 44 is arranged in a face-to-face relationship with the first housing member 12. The second housing member 42 has a plurality of standoffs 46 and a central standoff 47, in a manner similar to the first housing 12, disposed off of the inside surface thereof, as can be seen in FIG. 2. The peripheral wall 44 has an annular rim 22 extending radially therefrom. A sharp, energy directing sealing edge 24 extends off of the distal end of the annular ring 22, as shown in FIG. 2. The second generally circular vapor permeable membrane 34 is attached by known bonding means to the annular rim 22 on the distal edge of the peripheral wall 44. The sealing edge 24 forms the bonding material when the housings 12 and 42 are bonded together in a final assembly thereof. Prior to the final assembly, the flat disc-like heater 40 is sandwiched between the first and second membranes 28 and 34 which membranes then define the envelope in which the heater 40 is sealed, the lip 18, generally defining the perimeter of the envelope.

The heater 40 may be comprised of an etched foil type heater which is encapsulated in silicone rubber or other insulation and may have a wicking material attached by vulcanization or the like to its outer surface, to promote full wetting of its surface. The heater 40 is a type which may be purchased from MINCO Products, Inc. of Minneapolis, Minn.

Figure 4:
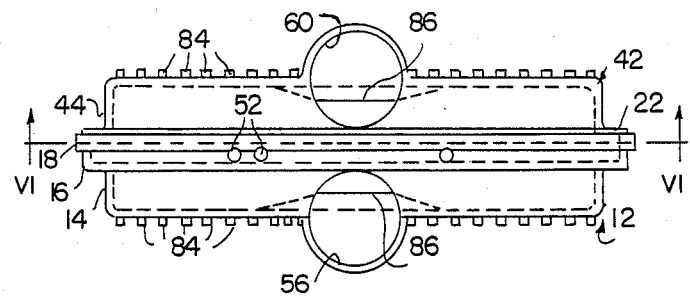
FIG. 4 is a view taken along the lines IV–IV of FIG. 2.

The heater 40 has a pair of electrical leads 50 which extend radically outwardly from an edge portion thereof, and through the envelope and a pair of watertight openings 52 which are disposed through the lip 18 of the shoulder 16, as shown in FIGS. 1 and 4, to a proper electrical power source, not shown.

A water supply conduit 54 is likewise arranged through the lip 18 of the shoulder 16 of the first housing member 12 with its distalmost end 55 sealingly received in the envelope defined by the peripherally sealed membranes 28 and 34 to permit water to be discharged into the envelope or pocket, as shown in FIGS. 1, 2 and 4.

The first housing member 12 has an inlet opening 56 and an outlet opening 58 arranged diametrically across from one another. The inlet and outlet openings 56 and 58 are in fluid communication with one another across the fluid flow chamber 26 defined between the first vapor permeable membrane 28 and the inner surface of the first housing member 12.

The second housing member 42 also has an inlet opening 60 and an outlet opening 62 arranged diametrically across from one another. The inlet and outlet openings 60 and 62 are also in fluid communication with one another across the fluid flow chamber defined between the second vapor permeable membrane 34 and the inner surface of the second housing member 42.

Figure 5:
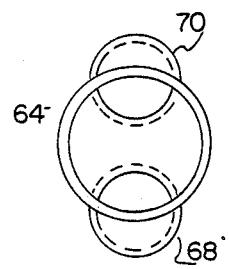
FIG. 5 is an end view of one of the port members.

The first and second housing members 12 and 42 are mated in a rim to rim manner as shown in FIG. 2, and a bifurcated junction 64 is mated with the inlet openings 56 and 60. The bifurcated inlet junction 64 is shown in FIGS. 2 and 5 comprising a channel 66 which splits into a pair of conduits 68 and 70 which each mate respectively with the inlet openings 56 and 60.

A bifurcated outlet 74 junction is shown on the left side of the assembly depicted in FIG. 2. The bifurcated outlet junction 74 comprises a pair of conduit 76 and 78 which join to form an outlet channel 80. The outlet channel 80 connects to a conduit, not shown, which typically leads to a patient being treated.

The second housing member 42 has a port 82 extending therethrough. The port 82 permits the installation of a temperature probe, not shown, which would be registered in a sealing relationship therewith.

Figure 6:
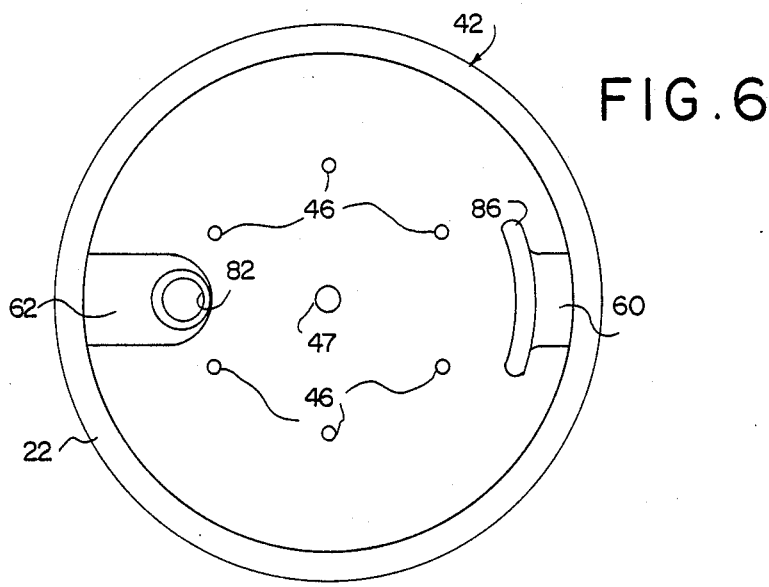
FIG. 6 is a view taken along the lines VI–VI of FIG. 4.

Each housing member 12 and 42 has a plurality of parallel fins 84 on the outer surface thereof, in a manner as shown in FIGS. 1, 2, 3 and 4. Each housing member 12 and 42 also has a cresent shaped vane 86 on the downstream peripheral edge of the inlet opening as shown in exemplary manner in FIG. 6. The vane 86 assists in the dispersal of the gas coming into the assembly from the gas source, to facilitate its mixing with the water vapor that emanates past the vapor permeable membrane.

Thus, what has been shown and described is a heating element which is contained in a water atmosphere in hermetically sealed envelope of a vapor permeable membrane, disposed across a housing. The envelope of vapor permeable membrane acts as a divider in the housing through which gas flows from a gas source to a patient requiring the treated gas.

A water conduit supplies a controlled flow of water through a wall of the housing and into the envelope to react with an electrical heater also in the envelope to generate water vapor which then driven out of the envelope and into the respective chambers between the envelope and each of the housing members, to be picked up by the separate gas flows and directed to the outlet and subsequently to the recipient. Since the heater is bathed in water in a hermetically sealed vapor permeable envelope, the housing containing the envelope need not be restricted to a "one position only" orientation, but can be utilized near the patient in any orientation, such as on its side, or tilted, or flat the nearness permitting less water and energy usage, a smaller temperature drop between humidifier and patient, less condensation in the conduit, and no likelihood of patient injury (drowning) by water passing into the conduit leading to the patient.

I claim:

1. An omniorientable humidifier assembly for humidifying a breathable gas, said humidifier assembly comprising:
   a hollow housing;
   a gas inlet means in said housing;
   a gas outlet means in said housing; and
   a vapor discharge means in said housing;
   said vapor discharge means arranged so as to define a plurality of flow paths in said housing between said gas inlet and said gas outlet means, whereby to maximize the vapor discharge capabilities of said humidifier assembly;
said gas inlet means comprising a bifurcated junction which directs gas from a conduit separately into said flow paths in said housing.

2. An omniorientable humidifier assembly for humidifying a breathable gas, said humidifier assembly comprising:
a hollow housing;
a gas inlet means in said housing;
a gas outlet means in said housing; and
a vapor discharge means in said housing;
said vapor discharge means arranged so as to define a plurality of flow paths in said housing between said gas inlet and said gas outlet means, whereby to maximize the vapor discharge capabilities of said humidifier assembly;
said gas outlet means comprising a bifurcated junction which receives treated gas from said plurality of flow paths in said housing into a common conduit for transmission to a patient.

3. A position independent humidifier apparatus, comprising:
a hollow housing;
as a vapor permeable enclosure arranged in said hollow housing;
a heater arranged in said vapor permeable enclosure;
a water supply means in communication with said vapor permeable enclosure; and
a gas inlet and a gas outlet each in communication with said hollow housing to direct gas over more than one surface of said vapor permeable enclosure, to optimize the heat-moisture transfer therefrom.

4. A position independent humidifier apparatus as recited in claim 3, wherein said vapor permeable enclosure comprises an envelope having at least two surfaces for effectuating said transfer of heat and moisture.

5. An omniorientable humidifier assembly for humidifying a breathable gas, said humidifier assembly comprising:
a hollow housing;
a gas inlet means in said housing;
a gas outlet means in said housing; and
a vapor discharge means in said housing;
said vapor discharge means arranged so as to define a plurality of flow paths in said housing between said gas inlet and said gas outlet means, whereby to maximize the vapor discharge capabilities of said humidifier assembly;
said vapor discharge means comprising a vapor permeable envelope having a heater and a water discharge means therein.

6. An omniorientable humidifier assembly as recited in claim 5, wherein said vapor permeable envelope comprises a first layer of vapor permeable membrane and a second layer of vapor permeable membrane hermetically sealed at their peripheral edges, said heater means being sandwiched between said first and second membranes.

7. An omniorientable humidifier assembly as recited in claim 5 wherein said vapor permeable envelope completely encloses said heater means.

8. An omniorientable humidifier assembly as recited in claim 5, wherein said water discharge means comprises a conduit which permits water to discharge into said envelope from a water source.

9. An omniorientable humidifier assembly as recited in claim 6 wherein said flow paths comprise the space between each vapor permeable membrane and its respective housing member.

10. An omniorientable humidifier assembly as recited in claim 6, wherein said vapor permeable membrane prevents liquid water from passing therethrough.

11. An omniorientable humidifier assembly as recited in claim 6, wherein said first layer and said second layer of vapor permeable membranes are each hermetically sealed to their respective housing member.

12. An omniorientable humidifier assembly as recited in claim 11 wherein each housing member has an annular lip against which said membranes are attached.

13. An omniorientable humidifier assembly as recited in claim 8, wherein said water conduit extends into said housing through an edge portion thereof.

14. A position independent humidifier apparatus, comprising;
a hollow housing;
a vapor permeable enclosure arranged in said hollow housing;
a heater arranged in said vapor permeable enclosure;
a water supply means in communication with said vapor permeable enclosure;
a gas inlet and a gas outlet each in communication with said hollow housing to direct gas from a source to the apparatus and from the apparatus to a patient, once the gas has been treated within the apparatus.

15. A position independent humidifier apparatus as recited in claim 14, wherein said water supply means discharges water into said enclosure for heating and transmission thereof through said vapor permeable enclosure.

16. A position independent humidifier apparatus as recited in claim 15, wherein said enclosure divides said hollow housing into two chambers, one on each side thereof.

17. A position independent humidifier apparatus as recited in claim 16 wherein a plurality of standoffs are arranged on the inner surface of said housing, to support said enclosure therewithin.

18. A position independent humidifier apparatus as recited in claim 17, including:
a plurality of fins arranged on the outer surface of said housing to facilitate cooling thereof.

19. A position independent humidifier apparatus as recited in claim 14, including a gas deflecting vane arranged on the inside of said housing downstream of said gas inlet, to disperse gas coming therein throughout said apparatus.

20. A position independent humidifier apparatus as recited in claim 14, wherein said hollow housing is of generally disc-like configuration, having a peripheral wall comprising the location of its juncture.

21. A position independent humidifier apparatus as recited in claim 20, wherein a port is disposed through said housing to facilitate temperature analysis of the gas within said housing.

22. A position independent humidifier apparatus comprising;
a pair of housing members having a peripheral wall therearound, to define a hollow housing;
a vapor permeable fluid impermeable enclosure arranged in said housing;
a heater arranged within said enclosure;

a water supply means arranged in communication with said enclosure; and a pair of gas passageways arranged in said housing and in communication with one another to permit gas brought into said housing to be treated by reaction with said enclosure and discharged out of said housing.

23. A position independent humidifier apparatus as recited in claim 22, including:

a divided junction arranged in communication with at least one of said gas passageways in said housing, to direct the flow of gas with respect to said housing.

24. A position independent humidifier apparatus as recited in claim 23, wherein said divided junction comprises a bifurcated connector attached to each of said gas passageways in said housing.

25. An omniorientable humidifier assembly for humidifying a breathable gas, said humidifier assembly comprising:

a hollow housing comprising a pair of housing members of disc-like configuration having peripheral walls which mate together;

a gas inlet means in said housing;

a gas outlet means in said housing; and a vapor discharge means in said housing;

said vapor discharge means arranged so as to define a plurality of flow paths in said housing between said gas inlet and said gas outlet means, whereby no maximize the vapor discharge capabilities of said humidifier assembly.

* * * * *